United States Patent [19]
Perkins et al.

[11] Patent Number: 5,442,180
[45] Date of Patent: Aug. 15, 1995

[54] APPARATUS FOR THE FIELD DETERMINATION OF CONCENTRATION OF RADIOACTIVE CONSTITUENTS IN A MEDIUM

[75] Inventors: Richard W. Perkins; Alan J. Schilk, both of Richland; Ray A. Warner, Benton City; Ned A. Wogman, Richland, all of Wash.

[73] Assignee: Battelle Memorial Institute, Richland, Wash.

[21] Appl. No.: 110,284

[22] Filed: Aug. 19, 1993

[51] Int. Cl.$^6$ .......................................... G01T 1/167
[52] U.S. Cl. ................... 250/367; 250/486.1
[58] Field of Search ............... 290/367, 368, 366, 369, 290/370.06, 486.1, 487.1

[56] References Cited

U.S. PATENT DOCUMENTS 4,362,946 12/1982 Cusano et al. ................... 250/367

OTHER PUBLICATIONS

Eckardt et al, "A Novel light-collection system for segmented scent.-count. calor," Nu. Inst. & Meth. vol. 155, No. 31978) p. 389.

Primary Examiner—Paul M. Dzierzynski
Assistant Examiner—Richard Hanig
Attorney, Agent, or Firm—Johnnie R. Hynson

[57] ABSTRACT

The instant invention is an apparatus for determining the concentration of radioactive constituents in a test sample; such as surface soils, via rapid real-time analyses, and direct readout on location utilizing a probe made up of multiple layers of detection material used in combination with an analyzer and real-time readout unit. This is accomplished by comparing the signal received from the probe, which can discriminate between types of radiation and energies with stored patterns that are based upon experimental results. This comparison can be used in the calibration of a readout display that reads out in real-time the concentrations of constituents per given volume. For example, the concentration of constituents such as Cs-137, Sr-90, U-238 in the soil, and noble gas radionuclides such as Kr-85 in the atmosphere, can be measured in real-time, on location, without the need for laboratory analysis of samples.

14 Claims, 12 Drawing Sheets

APPARATUS FOR THE FIELD DETERMINATION OF CONCENTRATION OF RADIOACTIVE CONSTITUENTS IN A MEDIUM

This invention was made with Government support under Contract DE-AC06-76RLO 1830, awarded by the U.S. Department of Energy. The Government has certain rights in the invention.

FIELD OF THE INVENTION

The present invention relates generally to an apparatus for determining the concentration of radioactive constituents (radionuclides) in a test sample (such as surface soil) via direct readout on location or remotely. More specifically, the invention utilizes a multi-layered probe and a data analysis unit that correlates the incidence of detections in multiple layers from a spectrum of nuclear radiation or from a single photon or particle. The invention can discriminate between energies and the types of radiation.

BACKGROUND OF THE INVENTION

One of the most important aspects of the regulation and remediation of radioactive constituents in the soil, or other media, is the accurate and cost effective determination of the concentration of these constituents. Currently, samples are taken on location and sent to laboratories for analysis. This is a costly and time-consuming process.

These environmental assessments will require the measurement of radionuclides that decay by the emission of $\alpha$, $\beta$, or $\gamma$ radiation. The current trend in permissible concentrations of radioactive constituents is toward lower concentrations. This has made it increasingly difficult to obtain measurements on location with portable instruments. The instant invention, with its higher sensitivity and ability to discriminate between types and energies of radiation, is therefore suited to accommodate this trend. It is even more difficult to obtain the concentration on location without expensive and fragile equipment used in a time-consuming process. Hence, there is a need for a rugged, fieldable, low-background, high-sensitivity, portable radiation detector that is capable of discriminating between energies and radiation types on the location of the medium, and on a real-time basis.

This trend also creates the need for measurement of radioactive constituents below that of current regulatory requirements. This is achievable by the instant invention.

When there is a radioactive event or disintegration of an unknown target constituent in the medium to be analyzed, it will cause a number of particles to be ejected at energies specific to the suspected target constituents. It should be noted that the words "particle" and "radiation" are used synonymously within this application.

SUMMARY OF THE INVENTION

The instant invention is an apparatus for determining the concentration of radioactive constituents in a test sample (such as surface soil) via real-time direct readout on location.

The instant invention utilizes a probe made up of multiple layers of detection material used in combination with the analysis unit and readout display. Electronic signals from the probe are carried by a connecting cable to an analysis unit. The analysis unit yields the type and concentration of constituents in the target sample, a solid medium, or gaseous sample. Within the analysis unit, the signal received from the probe is compared to recorded calibration data or a stored pattern within the analysis unit that is based upon prior experimental results. The stored data, the calibration data, and the prior experimental results, will confirm the direct correlation between a pattern of signals received in the probe, and a concentration of a radioactive constituent in a medium of known (calculated, estimated, extrapolated, or measured) concentration and spacial distribution. This correlation is used in calibration of a readout display that reads out in real-time in the concentration of constituents per given volume.

Specifically, when one of these particles passes through the probe, it will react with the different layers depending upon its energy and radiation type. The pattern of signals, or counts, is compared to stored signal patterns from a target of known constituents and spacial distribution, thereby identifying the concentration of the target constituent.

The probe is configured into various layers wherein each layer that interacts with a radioactive decay particle provides a detection or electric signal corresponding thereto.

This enables those patterns of interactions, in the form of detection or electrical signals that are due to certain constituents, to be identified. The number of counts per minute (cpm) is determined by totaling the counts and comparing them to a timing circuit that is readily available in the art. The typical unit of measurement is cpm.

By experimental determination, the amount of cpm for a given constituent, concentration, distribution, and configuration is determined for reference. This information is stored in the analyzer unit or used as data to calibrate the readout display of the analyzer unit; i.e., this reference pattern of counts can be compared to the pattern of counts coming from the probe. When a recognizable pattern is received by the analyzer unit, a signal can be generated that can cause a display to read the concentration of constituents in the target medium. This method of calibration will be necessary for each type of constituent and configuration of the test sample that is desired to be investigated.

For example, the concentration of constituents includes, but is not limited to, promethium-147, cesium-137, strontium-90, and uranium isotopes. Also, other radionuclides in the soil can be measured in real-time on location without the need for laboratory analysis of samples.

The top layer of the instant invention probe is able to detect cosmic radiation or other ionizing radiation from above and, through coincidence techniques, cancel these background effects. High-energy $\beta$ particles entering the sensor from an underlying area being interrogated can traverse several detector layers of the sensor. By requiring this unique signature and no events in other detector layers, the background for such measurements is minimized. Gamma rays entering the instant invention sensor have essentially an equal probability of producing an energetic electron in any layer of the instant invention probe, and therefore provide a unique signature. A very low-energy $\beta$ particle from an underlying surface will penetrate a smaller number of sensor layers and thus will produce a characteristic signature. An $\alpha$ particle will only penetrate a very thin (paper thin) sensor layer, but will produce a large, rather unique signal. Thus, because it discriminates by individual detection layer which signal it wishes to consider for different radioactive constituents, the background is greatly reduced and the sensitivity enhanced for the detection of lower levels than were previously achievable.

It is very useful to be able to simultaneously measure these radionuclides on a real-time basis at a sensitivity which permits a fraction of the concentrations permitted by regulations to be observed. The instant invention does away with the long periods of time now required for the sample to be sent to a lab for analysis.

Within this patent application, an individual release of energy or matter from a radioactive nucleus will be termed as a particle or as radiation. Alpha ($\alpha$) particles are particles that consist of two neutrons and two protons, and have a charge of +2. Beta ($\beta$) particles are used synonymously with electrons in most parts of this application. However, $\beta$ particles include both $\beta-$ and $\beta+$. $\beta-$ denotes negatively charged electrons, while $\beta+$ denotes positively-charged electrons or positrons. Gamma ($\gamma$) particles are packets of energy. Gamma rays, $\gamma$ particles, $\gamma$'s, X-rays, and photons are used synonymously throughout depending upon the use and the nature of the events and items being described.

The interaction of a given particle in a particular layer is referred to as an interaction event, or simply as an event. When a prescribed pattern of interaction events is achieved, it is referred to as a count.

The instant invention has a very low background noise with the analysis unit because of its layered construction and the coincidence and anti-coincidence requirements that can be imposed in registering a count indicative of a specific radioactive constituent.

The invention can be constructed to provide a very large sensing area to further enhance sensitivity. The probe used in the instant invention enables distinguishing between $\beta$ and $\gamma$ radiation, and selective measurement of radionuclides which decay by $\beta$ particle emission only based on their energy. The current method for measurement of radionuclides which emit only $\beta$ particles involves chemical separations followed by counting the emitted $\beta$ particles in the laboratories using shielded probes, while $\gamma$-decay radionuclides are measured by use of multi-channel analyzers. The instant invention will enable the distinguishing, on location, between $\beta$ and $\alpha$ radiations, and enable real-time analysis.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

BRIEF DESCRIPTION OF THE DRAWINGS

FIG. 8a is a cross-section of the cylindrical probe along lines 8a—8a.

FIG. 10 is a cross-section of the cylindrical probe along lines 10a—10a.

DESCRIPTION OF THE PREFERRED EMBODIMENTS

The instant invention is an apparatus for the on-location, real-time determination of the concentration of radioactive constituents in a medium. A first preferred embodiment is an apparatus for the determination of concentration for radioactive nuclide contamination in soil.

Figure 1:
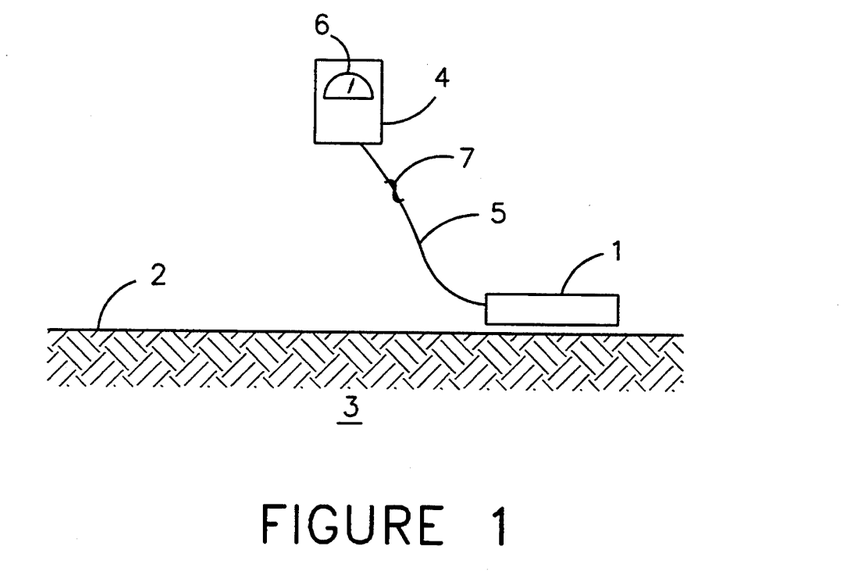
FIG. 1 is a schematic representation of the invention position to analyze an earthen surface.

FIG. 1 illustrates the use the first preferred embodiment of the instant invention. In this first preferred embodiment, a probe 1 is laid upon the surface 2 to be investigated; e.g., a test bed 3 and an analyzer unit 4 is connected to the probe 1 via a connecting cable 5. The readout display 6 on the analyzer unit 4 will read out directly the contaminant level in the test bed 3.

Typical contaminants that can be detected using the instant invention include, but are not limited to, Sr-90, U-238, Cs-137, Am-241, Pu-238, Pu-239, and Pu-240. Other radionuclides in soil, and noble gas radionuclides in the atmosphere, are also detectable with the present invention. Use of the instant invention is not limited to a test bed 3 of soil or to airborne inert radioactive gases. It is readily applicable to solid material or other media, as well as radioactive contaminated waste or materials placed inside a container.

The real-time readout capability of the instant invention is due to its unique ability to identify radiations of a particular energy, as well as to distinguish between types of radiations. Radiation is characterized by its source, type, and energy. For example, the daughter product of Sr-90 is Y-90, which decays by emission of a 2.29-MeV maximum-energy $\beta$ particle that could penetrate the entire thickness of most embodiments of the probe 1. The instant invention will be able to determine the approximate energy range and whether the radiation being detected is a $\alpha$, $\gamma$, or $\beta$ particle. From this information, the probe 1 can deduce the source of the radiation; i.e., the unknown target constituent. High-energy β's of this type can be discriminated from other β radiations by using the multi-layered detection means.

Figure 2:
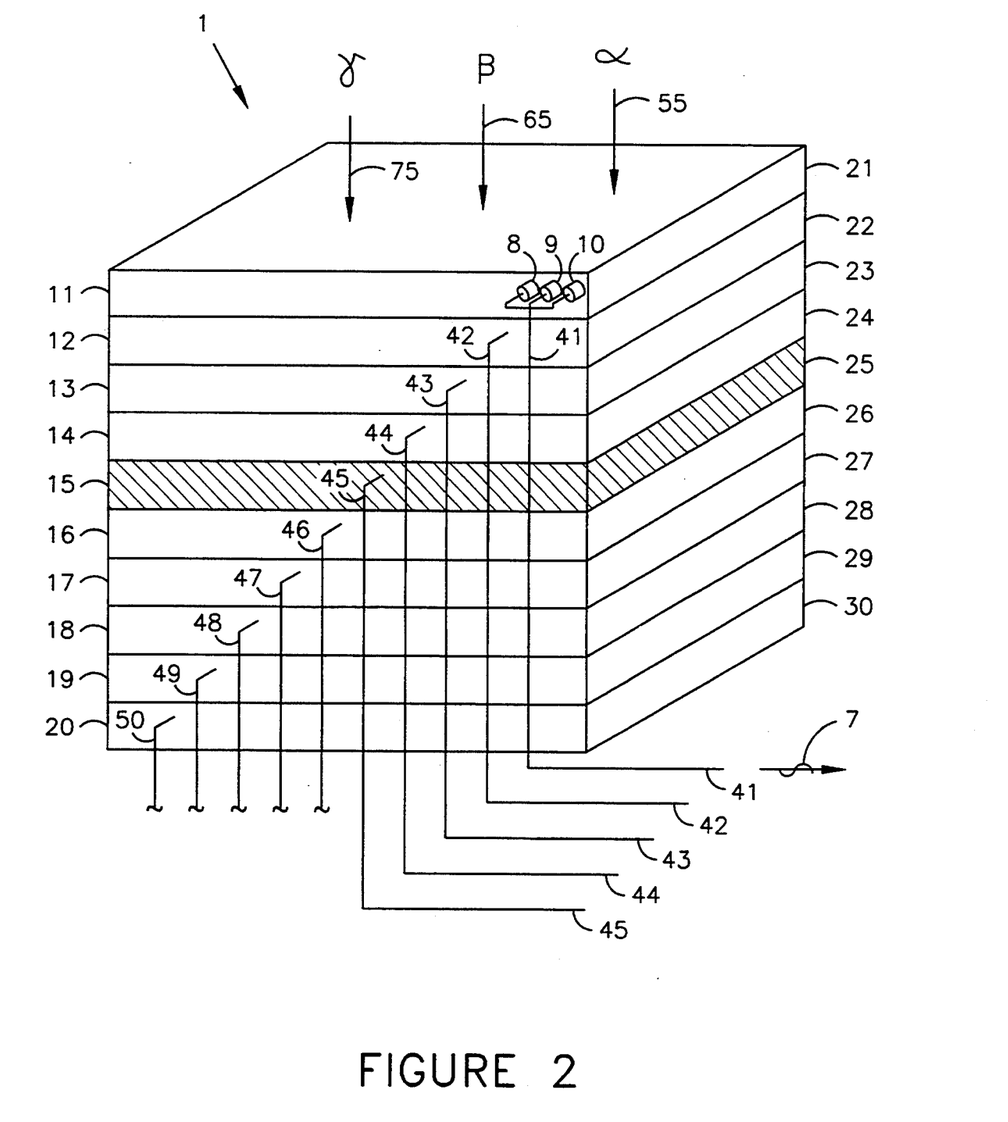
FIG. 2 is an isometric representation of the detection layers, the optical sensing assemblies, and the wiring connecting them.

As illustrated by FIG. 2, the probe 1 comprises optical sensing assemblies 8,9,10 connected to each of a plurality of detection layers 11-20 along the perimeters 21-30. For ease of illustration, the probe 1 is illustrated herein with a single array of optical sensing assemblies. It is to be appreciated that both ends of each of the detection layers 11-20 will be provided with such an assembly. The first preferred embodiment has optical sensing assemblies 8,9,10 located at opposite ends of each detection layer 11-20. It is preferred to keep the length of the detection layer 11 to under 2 meters, based upon the present art of fiber optics which has a half-length of about 2 meters. The width of the probe 1 is not limited and the width of a common roadway is clearly achievable and practical.

The instant invention can utilize a layer of any material that is capable of interacting with incident radiation and is referred to in general terms as a detection layer. The first preferred embodiment is constructed of organic scintillation material formed into layers. However, any material that produces a light signal in an interaction with incident radiation will perform as well. Additionally, an embodiment is possible that uses a material that does not produce light signals, but produces detection signals either directly or through an amplification means. The detection may or may not be converted to electrical signals for analysis.

Figure 3:
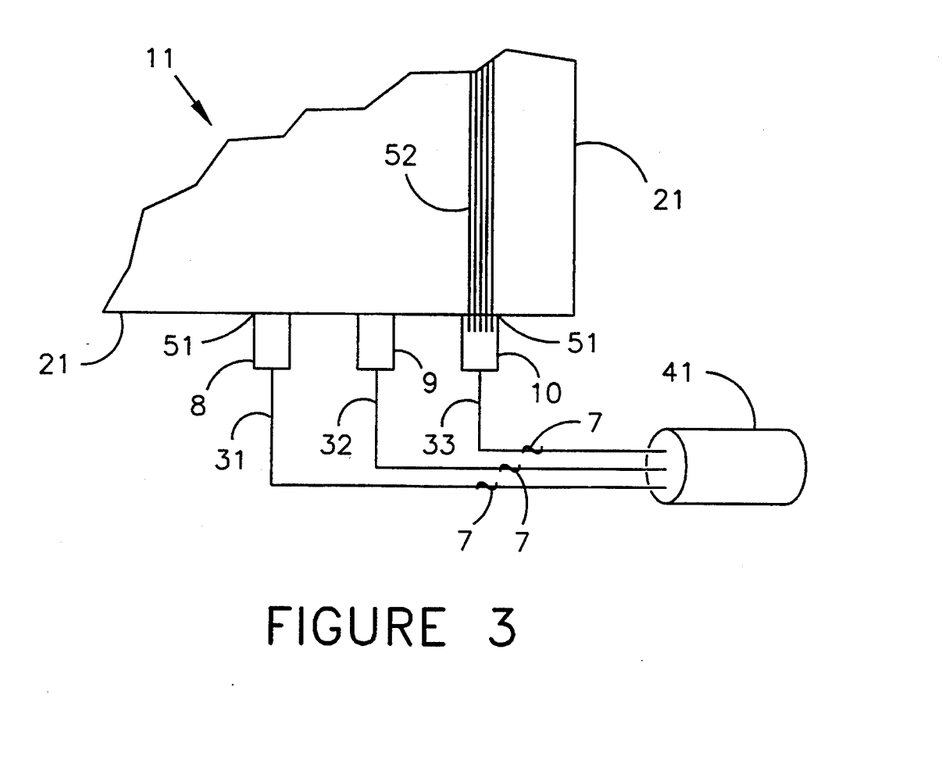
FIG. 3 is an enlarged portion of the area of the first detection layer at the point of attachment of the optical sensing assemblies.

FIG. 3 illustrates the first detection layer 11 that is typical of the other detection layers and has a plurality of optical sensing assemblies 8,9,10 attached to opposite ends of the detection layer perimeter 21. The number of optical sensing assemblies 8,9,10 is not critical to the invention. Applicant has found it useful to increase the number of optical sensing assemblies as the width of the probe 1 increases. The device illustrated herein is provided with three optical sensing assemblies only because a small unit was prepared for evaluation.

Each of the optical sensing assemblies 8,9,10 is attached to a signal lead 31,32,33 that carries the electrical signal 7 generated by the device. The assembly of the probe 1 is facilitated by grouping the signal leads 31,32,33 into a first signal lead grouping 41. Each of the detection layers 11-20 will have a signal lead grouping 41-50.

Figure 4:
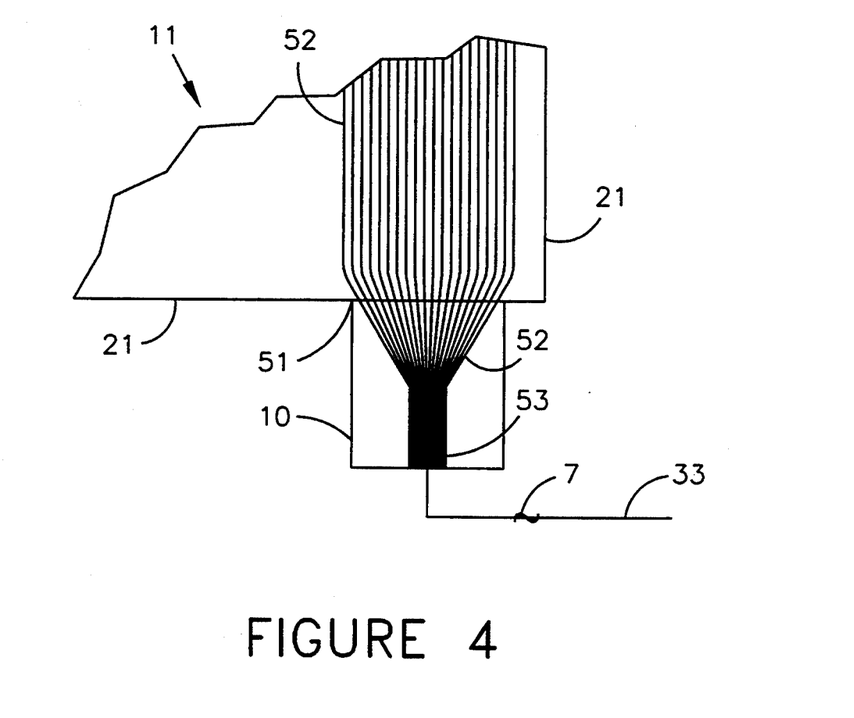
FIG. 4 is a cross section of an optical sensing assembly illustrating the fiber optical strands and the photomultiplier tube.

Within the optical sensing assembly 10, as illustrated in FIG. 4, is the means for converting a light signal into an electrical signal 7. An interaction of radiation with the detection layer 11 will cause light to be generated; this light will be collected by fiber optic strands 52 which can also serve as a detection layer 11, and directed to a photomultiplier tube 53 which converts the light to an electrical signal 7. A solid state photodiode is also adaptable to the instant invention in the place of the photomultiplier tube 53.

The fiber optic strands 52 are long strands typically of organic scintillation material that span the width of the probe 1, are gathered at a collection point 51, and have a sensing assembly 8 attached to each end.

While a photomultiplier tube 53 is currently the preferred means to convert light into electrical signals 7, there exists in the art several other means for generation of the required electrical signals 7 from a light source. The electrical signal 7 is picked up by a first signal lead 33.

The first preferred embodiment of the instant invention was constructed for the discrimination of a 1-MeV β in a probe 1 that comprises five detection layers 11-15 of grouped organic scintillation strands. Each of the embodiments that are specifically designed to detect an expected set of radiations will be constructed in typically the same manner, and generally of the same material. Embodiments are possible that use different materials within the plurality of layers that make up the probe. For example, a flat plat of organic scintillation material is clearly adaptable to the instant invention.

Other embodiments may have up to ten layers of scintillation material 11-20. To each of the opposing ends of these detection layers are attached a plurality of optical sensing assemblies 8,9,10.

Alpha Particle Analysis

It is well known in the art that α particles can only penetrate to a very shallow depth in most materials due to their massive atomic weight and high charge. The invention disclosed above applies to the detection of alpha particles as well. This is done by controlling the thickness of the detection layers, but to a much narrower thickness. A probe 1 for the detection of α particles would be covered with an extremely thin light-tight covering such as multiple thin layers of aluminized film, whereas those probes 1 used for the detection of β and γ radiation would be covered with a much thicker protective material. The first detection layer 21 of the probe 1 of the instant invention is much thinner, but not exceeding the penetrating range of the highly-ionizing α particles which produce very large signals in the thin layer compared to those from β particles and γ rays.

Figure 5:
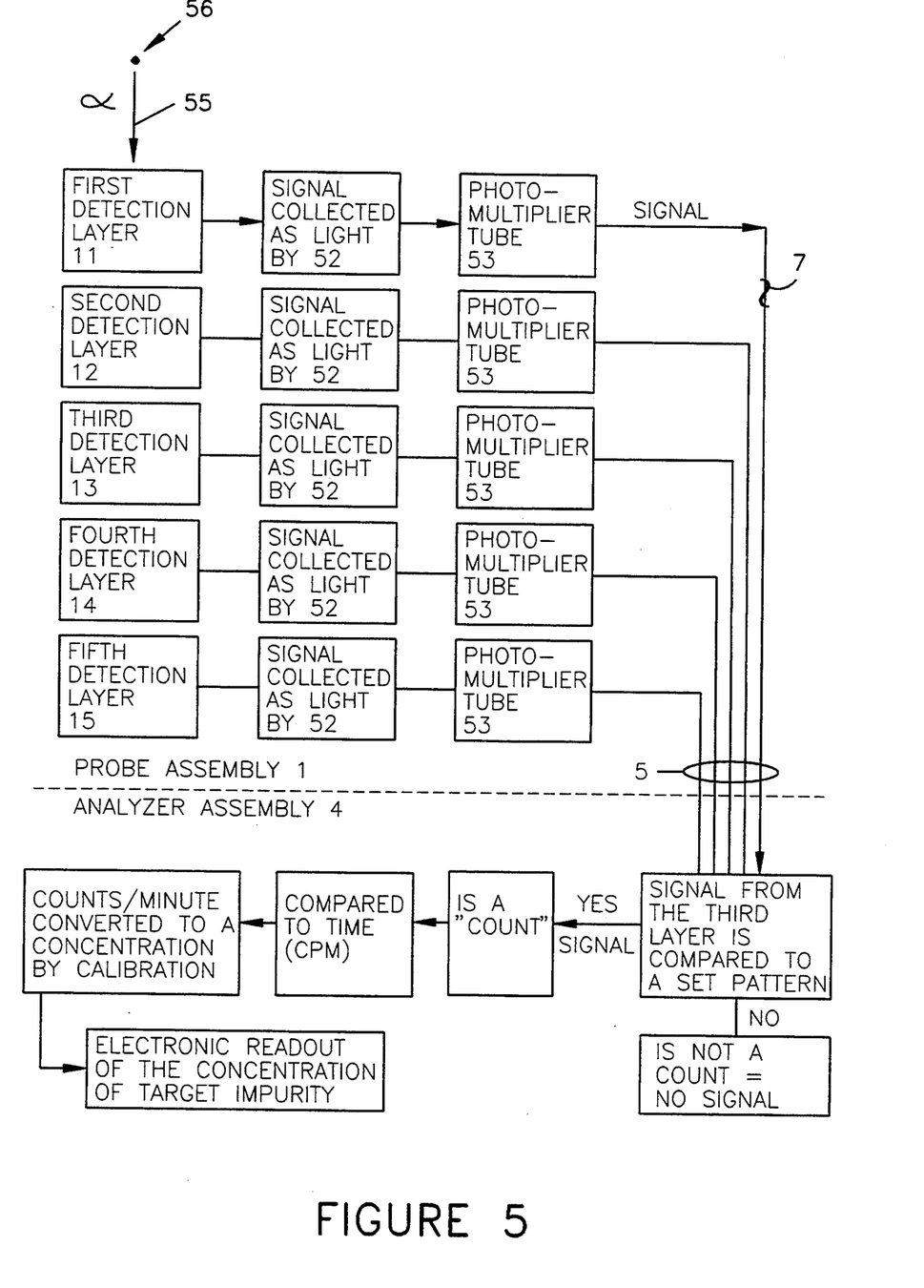
FIG. 5 is a block diagram that illustrates the analysis process of an $\alpha$-induced signal received from the probe assembly.
Figure 5A:
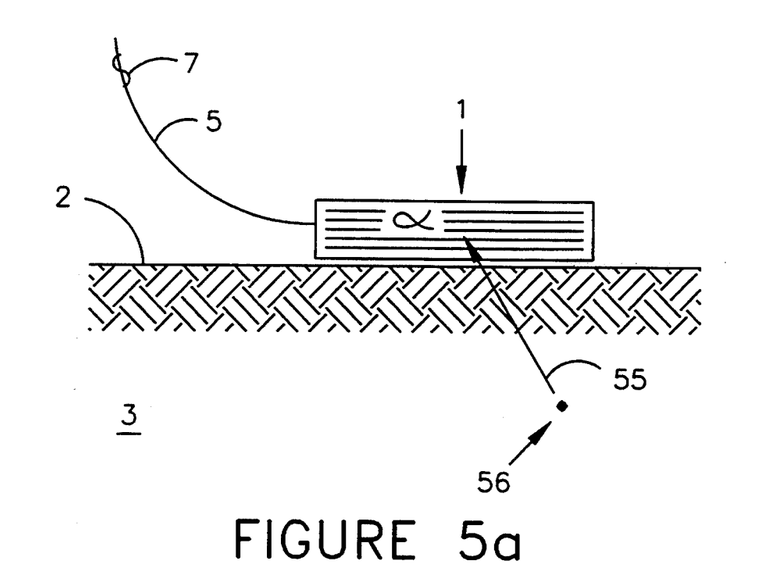
FIG. 5a is a schematic representation of the invention positioned to analyze an earthen surface that contains an $\alpha$-emitting radionuclide.

FIG. 5 traces the path of an electrical signal 7 through the apparatus that is caused by an α particle 55 generated from a radioactive nuclide 56 in the test bed 3 as illustrated on FIG. 5a.

Processing of a β-Radiation Event

Figure 6:
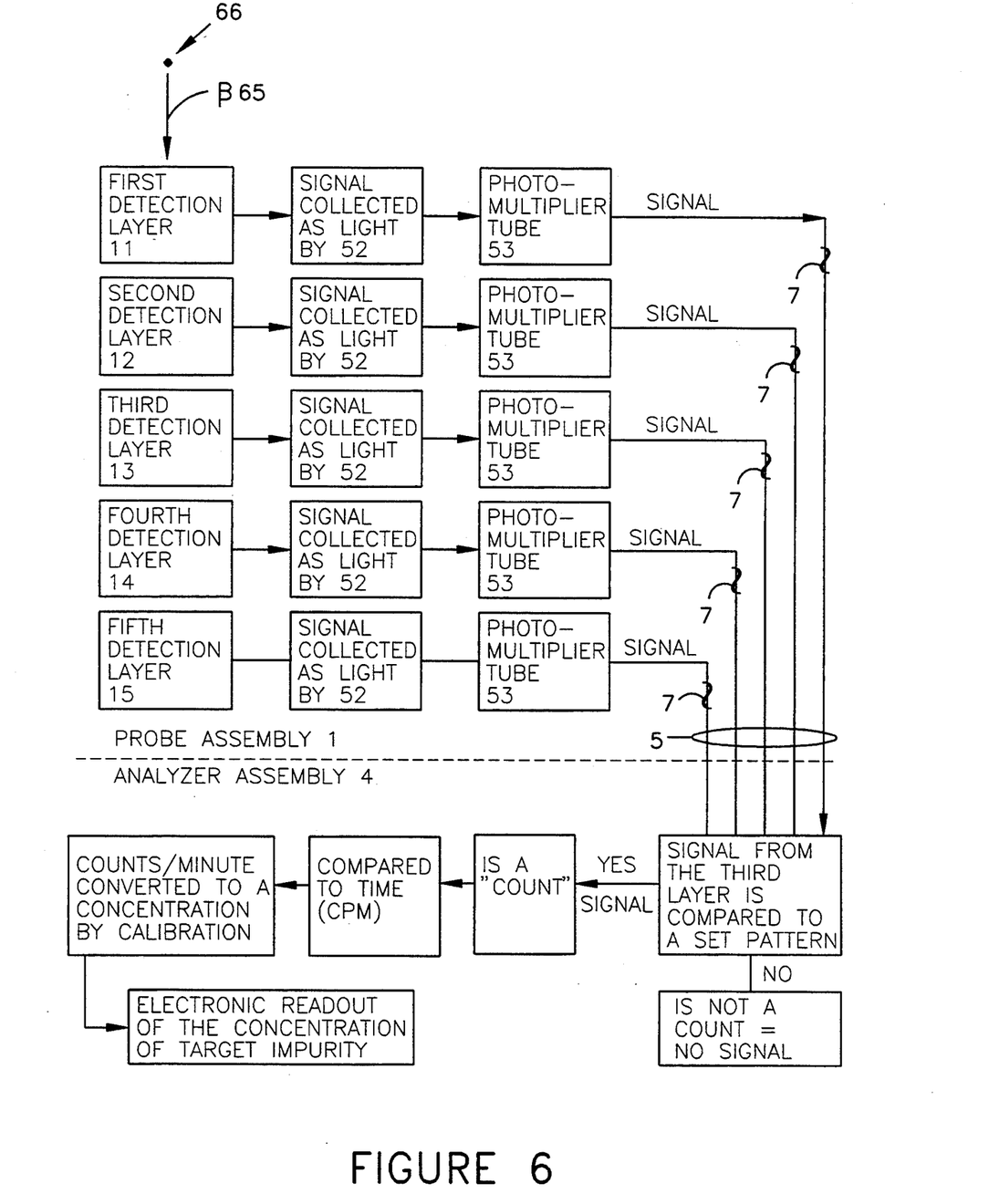
FIG. 6 is a block diagram that illustrates the analysis process of a $\beta$ signal received from the probe assembly.
Figure 6A:
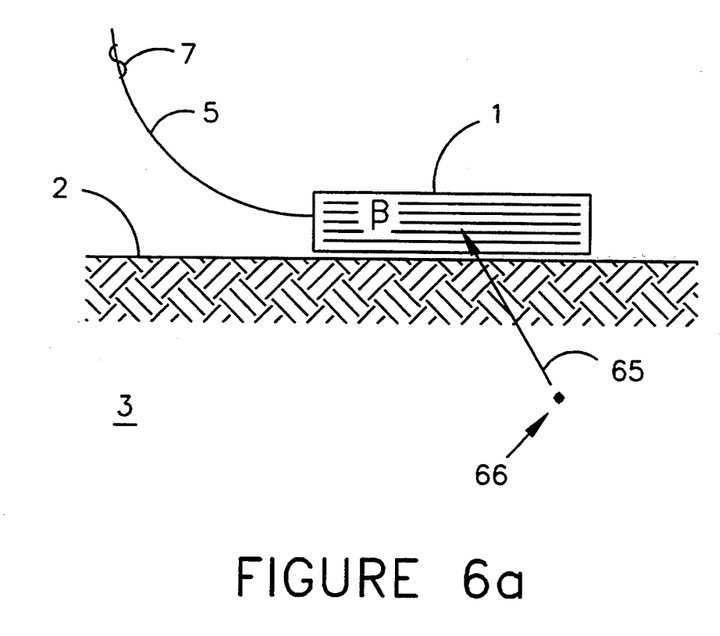
FIG. 6a is a schematic representation of the invention positioned to analyze an earthen surface that contains a $\beta$-emitting radionuclide.

FIG. 6 traces the path of an electrical signal 7 through the apparatus. This is caused by a β particle 65 generated from a radioactive nuclide 66 in the test bed 3, as illustrated in FIG. 6a.

For purposes of illustration, assume that the test bed 3 is contaminated with Sr-90, including its daughter Y-90, collectively represented as a single radioactive nuclide 66. This nuclide decays by emission of a 2.29-MeV maximum-energy β particle.

Probe 1 is placed upon the surface 2 of the test bed 3. The user can read the concentration of the Sr-90 on the readout display 6 of the analyzer unit 4. In the first preferred embodiment, the analyzer unit 4 is hand held by the user, with a connecting cable 5 leading to the probe 1. Other envisioned embodiments include the analyzer unit 4 and the probe 1 being physically connected by a stiff member (not shown) that may facilitate easier handling for some uses. Remote location of the analyzer unit 4 from the probe 1 is only limited by the transmission of the detection or electrical signals to the analyzer unit 4.

One disintegration of Y-90 (the daughter of Sr-90) will be discussed to illustrate the operation of the first preferred embodiment. One atom of Y-90 66 will be found a short distance under the surface of the test bed 3. Decay of a Y-90 atom causes the emission of a β particle 65 which travels through the test bed 3 soil and into the probe 1. This does not imply that all disintegrations of Y-90 should result in a β particle 65 passing through the probe 1. This "efficiency" is accounted for in the method of calibration of detector systems that is very well known in the art.

Calibration is the determination of a base signal pattern for the comparison of electrical signals 7 in the test bed 3. Calibration of the instant invention relies on the fact that there are a limited number of radioactive nuclides and that the radioactive decay of a specific element yields predictable radiation types with predictable energies. Also inherent in the calibration is the history of the soil beds to be examined. It is useful in determining what constituents are to be expected, as well as give the expected distribution of the target nuclide in the soil. Given sufficient memory space in the analyzer unit 4, enough experimental data can be stored to allow for the one-time calibration for all expected constituents.

As mentioned earlier, FIGS. 2 and 3 illustrate that to each detection layer 11, for example, is connected a plurality of optical sensing assemblies 8,9,10. Within each optical sensing assembly 10, for example, the light generated by a interaction is converted into an electrical signal 7.

Referring to FIG. 4, an energetic $\beta$ particle will react with a first detection layer 11 and subsequent detection layers. The resulting light pulses will be collected by the fiber optic strands 52 and delivered to the photomultiplier tube 53. The photomultiplier tube 53 will then produce an electrical signal 7 which will pass to the analyzer unit 4 via the connecting cable 5. The analyzer unit 4 will determine how many of the counts were received by any detection layer that meet the design criteria per unit time. This data will be compared to information stored within the analyzer unit 4, or will be used to produce a readout such that when compared to gathered data the concentration of Sr-90 will be determined.

2.29 MeV-$\beta$ Example

A 2.29-MeV maximum energy $\beta$ radiation has an average energy of about 0.8 MeV and will interact with the first three or four detection layers 11-14 a predictable fraction of the time depending on its distribution in the media being interrogated. This particular $\beta$ particle can be differentiated from $\gamma$ or X-rays since it has essentially an equal probability of producing ionization events and scintillation light in any of the layers of the scintillation material; i.e., the first detection layer 11 or one of the four latter detection layers 12-15. Each of the detection layers are approximately 1 mm in thickness. Gamma-ray detection principles actually detect the Compton or photoelectrons produced by a $\gamma$ interacting with matter. The useful data is the pattern of signals.

Low-Energy $\gamma$ Examples

Figure 7:
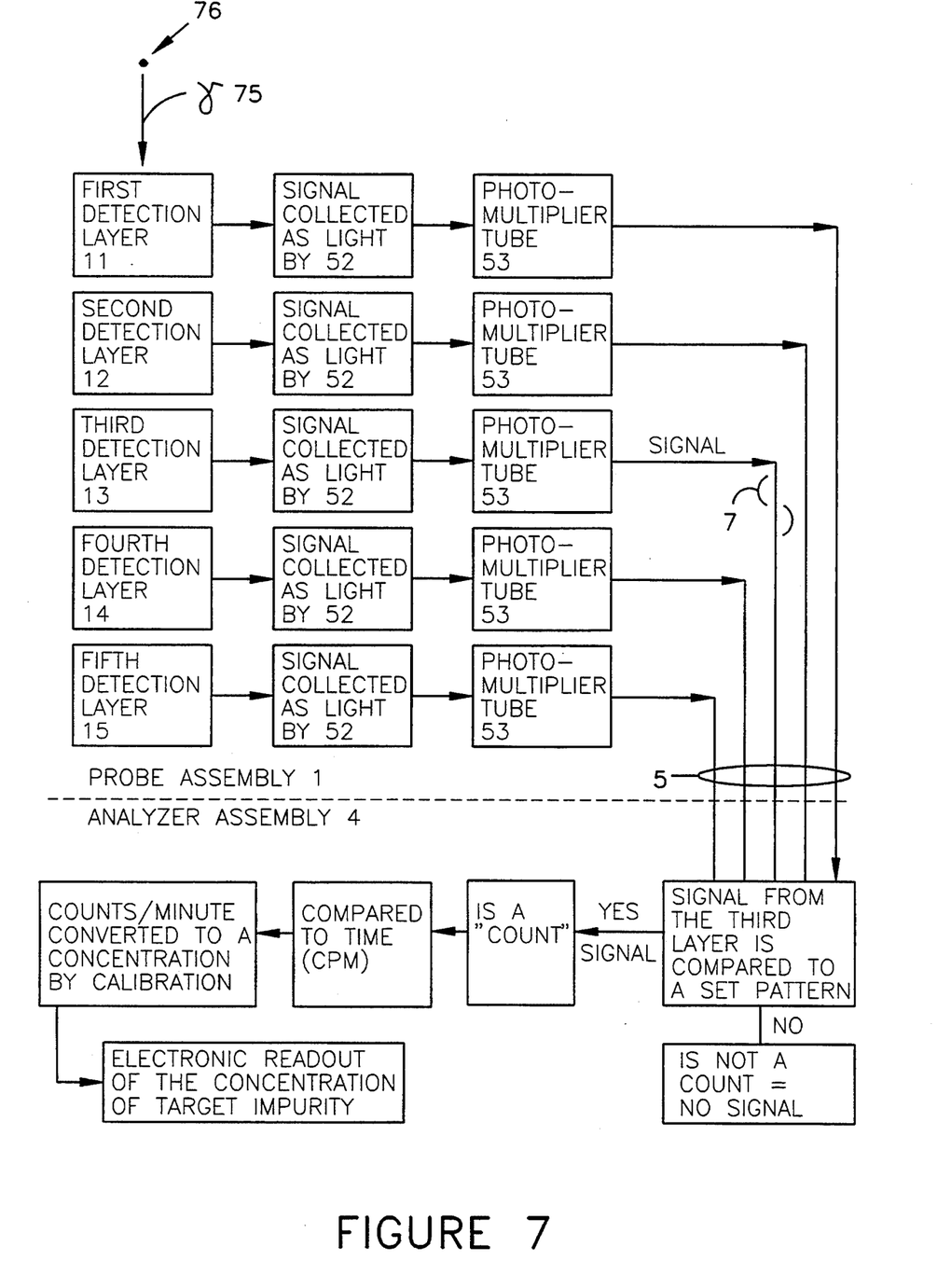
FIG. 7 is a block diagram that illustrates the analysis process of a $\gamma$ signal received from the probe assembly.
Figure 7A:
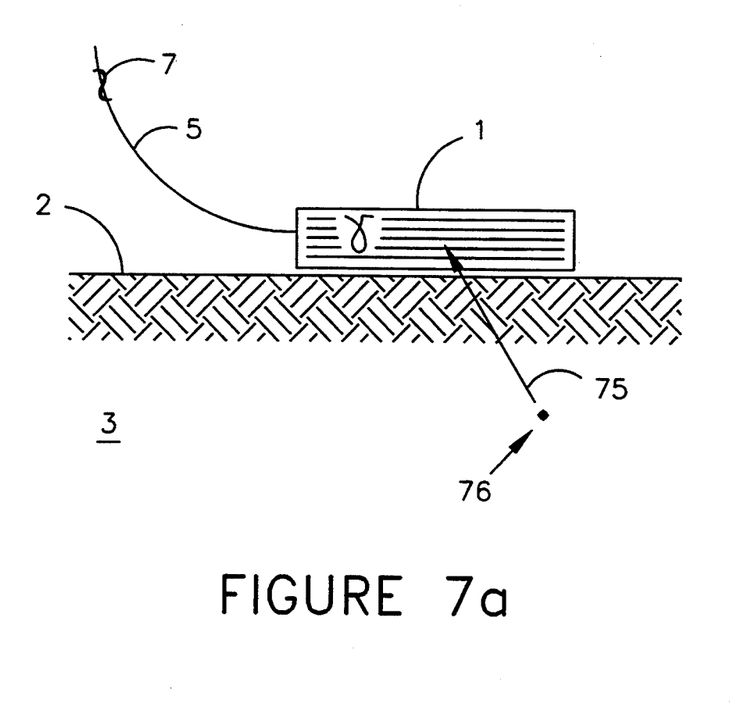
FIG. 7a is a schematic representation of the invention positioned to analyze an earthen surface that contains a $\gamma$-emitting radionuclide.

FIGS. 7 and 7a illustrate the detection of $\gamma$ radiation using the first preferred embodiment of the instant invention.

A low-energy $\gamma$, for example the 17.8-keV X-ray from the decay of plutonium, will have a path length in the scintillation layers which is sufficient to traverse ten 1-mm layers; however, the path length of the photoelectron, which will be produced in a layer where photoelectric capture of the X-ray occurred, will only be 0.01 mm. That interaction will therefore be restricted to one detection layer only, and the light signal produced in the layer will be very small compared with those produced from higher-energy $\gamma$ rays. Therefore, the 17.8-keV photon associated with plutonium decay will produce a very small scintillation event in only one layer.

For example, the detection layer 13 shown in FIG. 7 is a block diagram that traces the path of an electrical signal 7 caused by such activity.

Similarly, the Am-241 $\gamma$ of 59.5 keV could penetrate the entire thickness of most embodiments of the probe 1, and has a half-thickness in organic scintillator material of 30 mm. However, any Compton or photoelectron produced will expend all of its energy within 0.06 mm and also will, therefore, typically expend its energy within a single detection layer 11-15. However, its higher energy can permit distinguishing this event from a 17.8-keV signal.

High-Energy $\gamma$ Examples

A high-energy $\gamma$, for example the 662-keV photon from the decay of Cs-137, will have a path length well beyond the detection layers of the probe 1, but when an interaction does occur, it is likely to occur in one layer or another. Also, the most likely type of interaction will be a Compton event where the average energy of the resulting electron will be about half the energy of the original $\gamma$ ray with a path length of about 0.8 mm. It could, therefore, never interact with more than two layers of the probe 1. An interaction with one or two layers other than the first will indicate a $\gamma$ event and will, in most cases, only generate a signal in one layer; for example, the detection layer 13 as illustrated in FIG. 7 which is a block diagram that traces the path of an electrical signal 7 caused by a photon interaction where just one layer is involved.

Discrimination Between $\beta$ and $\gamma$ Radiation

The discrimination ability in the first preferred embodiment lies in the fact that a $\gamma$ ray may produce a signal in the succeeding detection layers 12-14 without producing a signal in the first detection layer 11. A $\beta$ particle from an underlying source will always produce a signal in the first detection layer 11. If the $\beta$ has sufficient energy, it could produce signals in additional detection layers as well, but in a predictable pattern. The instant invention thus permits clear distinction between $\beta$ sources and $\gamma$-ray sources as will be further explained.

Discrimination of Particles and Energy and Conversion into Real-Time Readout Discrimination requires three logical steps; the order of the first two steps is unimportant. First, is the determination as to the type of particle; i.e., is it an $\alpha$, $\beta$, or $\gamma$ particle. Secondly, the approximate energy of the particle must be determined. And finally, the source of the isolated radiation can be determined. The information about the uniqueness of radiation from a specific radionuclide is well known and readily available in the art. See Chart of the Nuclides, General Electric, Knolls Atomic Power Laboratory, August 1989.

The manipulation of the data can be accomplished by two preferred methods: 1) by using software, hardware, or a combination of both, located within the analyzer unit 4 itself, and 2) via calibration under known conditions. Both of these have as their basis the relationship of the flux of radiation particles with a specified energy being emitted from the surface of the test bed 3 to the radionuclide within the test bed 3.

For a specific example, consider that under known conditions the Sr-90 content of surface soil is 50 pCi per gram to a depth of a few centimeters or more. The signals from the first three or four layers of the probe 1 will indicate the emission of high-energy $\beta$ particles, and the number of counts per unit time above the background will indicate the concentration present in the soil.

It should be noted that the remediation and assessment of a radioactively contaminated area generally involves predictable impurities. This is because the history of the site is usually known, thus making calibration for expected conditions possible. Additionally, should prediction be difficult, then calibration will still be possible under controlled experimental conditions.

As mentioned earlier, the information gained can be stored in the analyzer unit 4 in software, hardware, or by calibrated settings.

Analysis of Specific Energy Ranges

The application of the instant invention covers $\beta$ energies of 10 keV and higher. The energy range for photons is similar. Discrimination between these types of particles is possible through this energy range.

The ranges can be extended downward as thinner and more sensitive large-area sensor materials become available.

It should be noted that these various embodiments for the specific applications will be accomplished by varying the thicknesses of the detection layers, the number of detection layers, and the interaction counting techniques.

Processing of a $\gamma$-Radiation Event

Returning to FIGS. 7 and 7a, a 0.662-MeV energy $\gamma$ ray 75 will be released when an atom of Cs-137 76 decays within the test bed 3. For ease of illustration, the $\gamma$ ray 75 will enter at the top portion of detection layers shown and travel towards the bottom of the detection layers illustrated in FIG. 2. On location, the radiation will travel from the medium up through the probe 1. This $\gamma$ ray 75 may not react with the first detection layer 11; however, it may cause ionization in one, or possibly two, adjacent detection layers 11-20. This ionization will cause light to be produced in those detection layer(s), and that light will be directed to an optical sensing assembly 10 on the perimeter 21-30. Within the optical sensing assembly 10, the light will be directed by the fiber optic strands 52 to a photomultiplier tube 53 which will cause an electrical signal 7 to be generated.

As shown in FIG. 7, the first detection layer 11 does not send a signal, but other detection layers 12-15 may send electrical signals 7 via leads 42-49 to the analyzer unit 4 via the connecting cable 5. Within the analyzer unit 4, the signal will be processed.

In the analyzer unit 4 will be a means to process the data that the first detection layer had no electrical signal 7, and that one or two adjacent detection layers had electrical signals 7 to constitute a $\gamma$-ray count. The analyzer will then determine the cpm via a means within the analyzer unit 4 or via calibration readout, and hence the concentration of the radioactive constituent in the test bed 3.

Analysis of Gaseous or Airborne Samples

A second preferred embodiment of the instant invention is for the analysis of gaseous or airborne radionuclides. The operation is similar to the first preferred embodiments except for the configuration of the probe 1.

Figure 8:
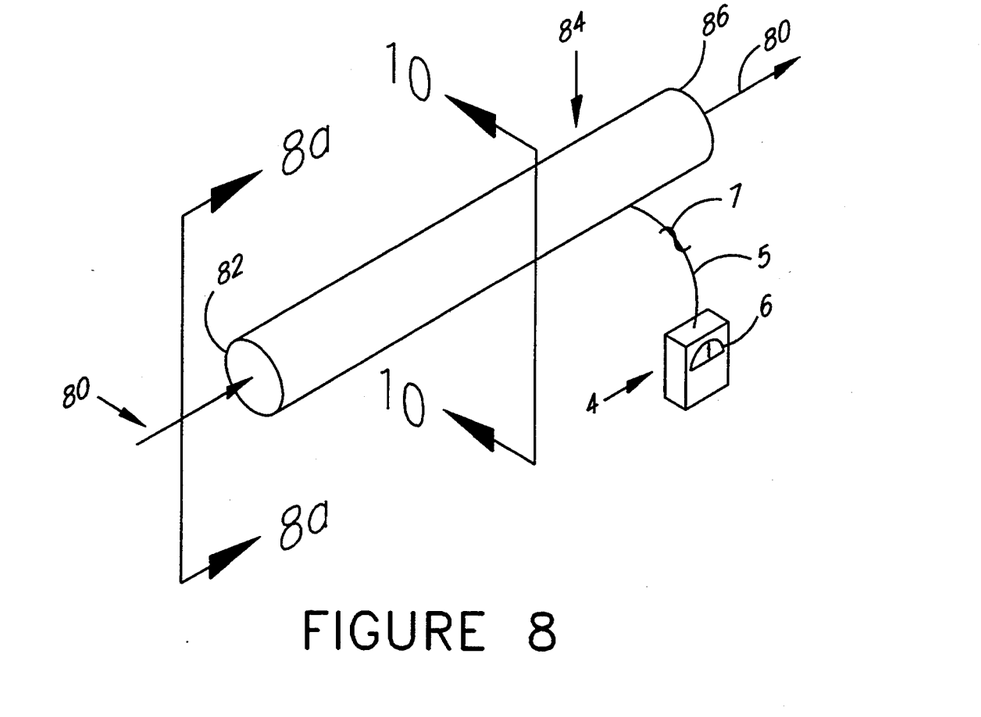
FIG. 8 is an isometric view of the cylindrical probe embodiment of the instant invention.

FIG. 8 is a schematic diagram of the second preferred embodiment which is suited to noble gas and airborne radionuclide concentration determination. The test fluid 80 to be analyzed containing noble gas or airborne radionuclides enters at the receiving end 82 of the cylindrical probe 84 and exits through the exit end 86. The cylindrical probe 84 is made up of layers of concentric cylinders.

Figure 8A:
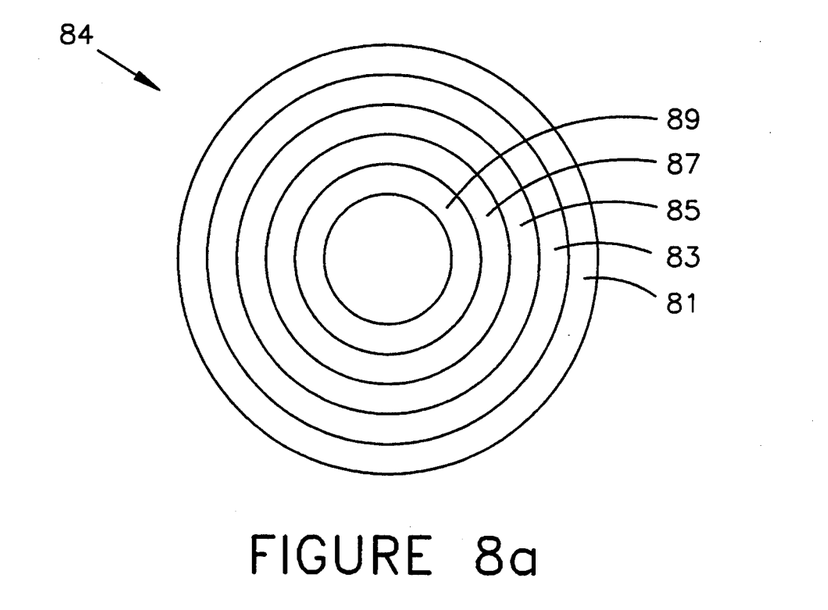
Figure 9:
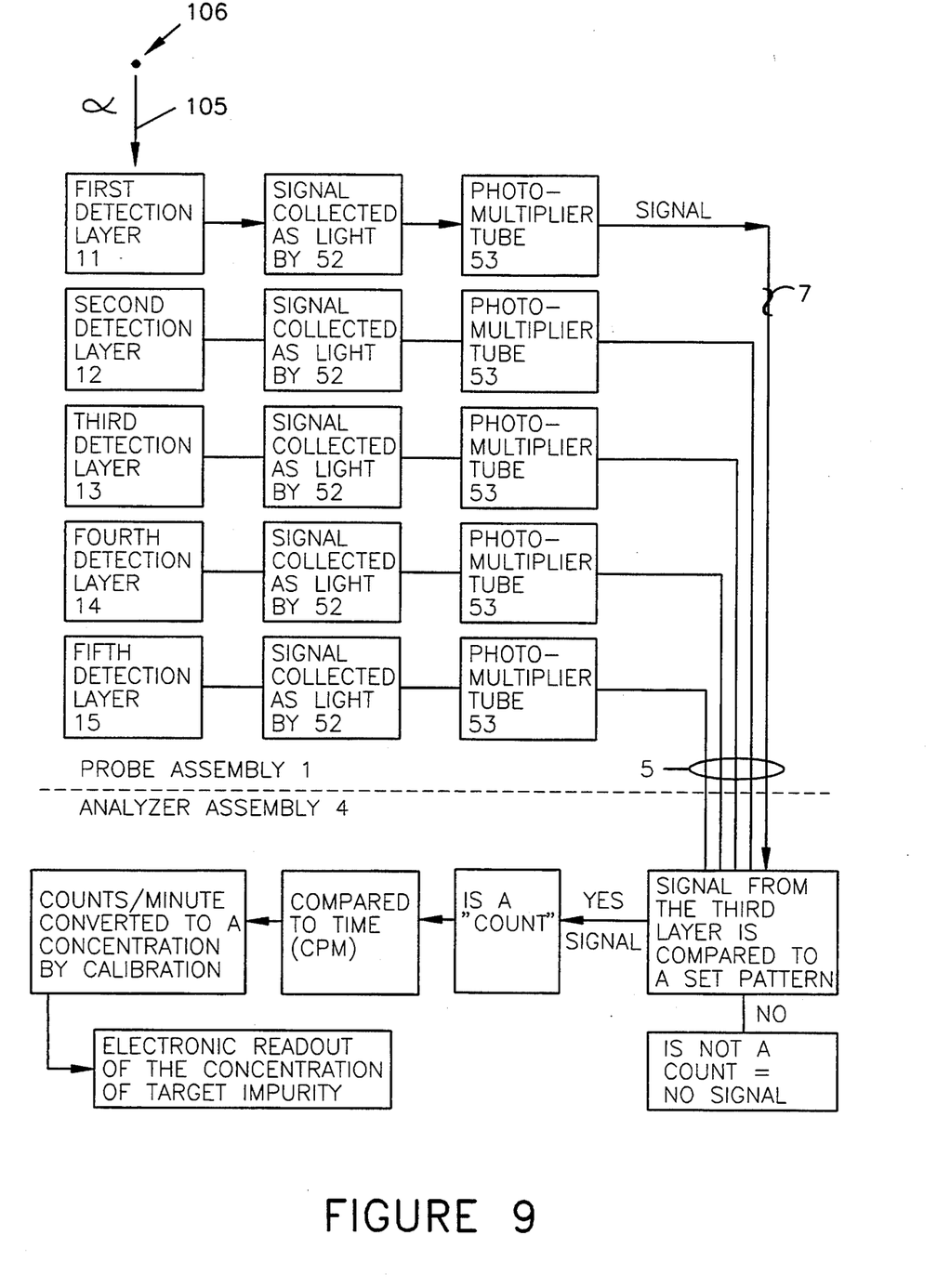
FIG. 9 is a block diagram that illustrates the analysis process of an $\alpha$ signal received from the cylindrical embodiment of the probe assembly.
Figure 10:
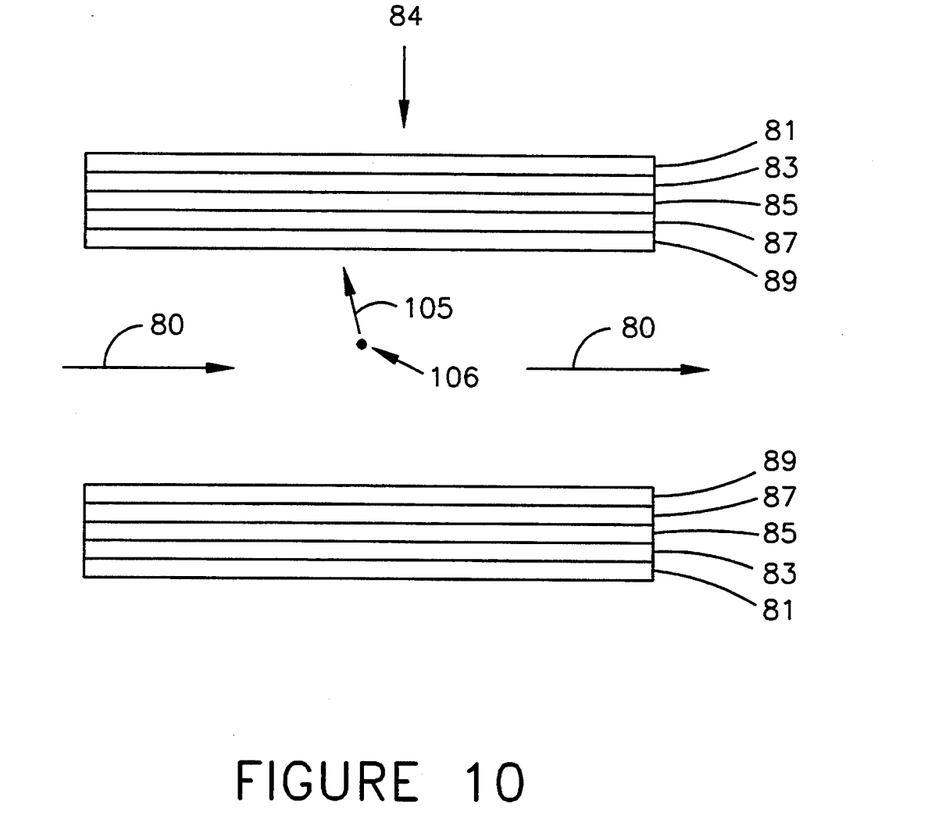

FIG. 8a is a cross-sectional view of the cylindrical probe 84 that illustrates the concentric relationship of the detection layers 81,83,85,87,89. Other than the physical configuration of the probe 84, all characteristics of the concentric cylindrical detection layers will be the same as the flat probe 1 discussed above. FIG. 9 illustrates what will happen when an energetic $\alpha$ particle reacts with the first detection layer 89 and not with subsequent detection layers. From FIG. 10 it will be apparent that when a radioactive nuclide 106 undergoes decay it will emit an $\alpha$ particle that will strike the first detection layer 89. Referring again to FIG. 9, the resulting light pulses will be collected by the fiber optic strands 52 and delivered to the photomultiplier tube 53. The photomultiplier tube 53 will then produce an electrical signal 7 which will pass to the analyzer unit 4 via the connecting cable 5. The analyzer unit 4 will determine that this was an $\alpha$ particle by comparison to stored patterns, and this information will be used to produce a readout such that when compared to gathered data the concentration of the constituents in the test fluid 80 will be determined.

This second preferred embodiment is useful in the real-time analysis of noble gas and airborne radionuclides, and is particularly suited for the analysis of samples containing constituents such as Kr-85. This second preferred embodiment for the determination of test fluids 80 is superior to current art in that it can discriminate on location between the energies and types of radiation coming from the test fluid 80. As in the first preferred embodiments, this apparatus can yield an accurate determination of concentration of radioactive constituents in the gaseous sample.

Other Embodiments Possible

The most readily applicable embodiments of the present invention are for $\alpha$, $\beta$, and $\gamma$ radiation. However, it should be noted that the instant invention includes embodiments that are sensitive to $\beta+$ and other charged particles as well.

While several embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. An apparatus for the on-location determination of the concentration of radioactive constituents in a medium comprising:
   (a) a probe having a plurality of detection layers for interacting with radioactive particles and producing a detection signal;
   (b) means for converting the detection signal into electrical signals, said means attached to said detection layers;
   (c) means for sending said electrical signal to an analyzer unit;
   (d) said analyzer unit comprising;
      (i) means for receiving said electrical signal, (ii) means for comparing the received electrical signal to a stored calibration signal pattern, and (e) a readout display for displaying comparison results;

whereby said readout display indicates the concentration or type of radioactive constituents in the medium.

2. The apparatus of claim 1, wherein the detection layers are constructed of organic scintillation material.

3. The apparatus of claim 1, wherein the means for converting the detection signal generated by an interaction with radiation into electrical signals is a photomultiplier tube.

4. The apparatus of claim 1, wherein the means for converting the detection signal generated by an interaction with radiation into electrical signals is a solid-state photodiode.

5. The apparatus of claim 1, wherein the means for sending is a connecting cable.

6. The apparatus of claim 1, wherein the detection layers are flat layers adjacent to one another.

7. The apparatus of claim 1, wherein the detection layers are detection layers of concentric cylinders.

8. The apparatus of claim 1, wherein the analyzer unit receives and analyzes the detection signal directly.

9. A method for the on-location determination of the type and concentration of radioactive constituents in a medium comprising the steps of:

(a) providing a probe having a plurality of detection layers, said detection layers interacting with radioactive particles and producing a plurality of detection signals;

(b) converting the detection signal generated into electrical signals;

(c) sending said electrical signals to an analyzer unit;

(d) comparing said electrical signals to stored calibration signals; and (e) displaying the results of step (d) as a readout on a display showing the type or concentration of radioactive constituents in the medium.

10. The method of claim 9, further comprising providing the detection layers of an organic scintillation material.

11. The method of claim 9, further comprising converting the detection signal generated by the interaction with radiation into electrical signals with a photomultiplier tube.

12. The method of claim 9, further comprising converting the detection signal generated by the interaction with radiation into electrical signals with a solid state photodiode.

13. The method of claim 9, further comprising connecting to the probe via a connecting cable.

14. The method of claim 9, further comprising providing detection layers in the form of concentric cylinders.

* * * * *